(12) United States Patent
Gill et al.

(10) Patent No.: US 7,686,938 B2
(45) Date of Patent: Mar. 30, 2010

(54) QUANTITATIVE, REAL TIME MEASUREMENTS OF LOCALIZED CORROSION EVENTS

(75) Inventors: Raymond Paul Gill, Grange over Sands (GB); Vladimir Jovancicevic, Richmond, TX (US); Wai Yeung Mok, Manchester (GB); Paul Hammonds, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 1185 days.

(21) Appl. No.: 11/262,861

(22) Filed: Oct. 31, 2005

(65) Prior Publication Data

US 2006/0144719 A1 Jul. 6, 2006

Related U.S. Application Data

(63) Continuation-in-part of application No. 11/086,191, filed on Mar. 21, 2005, now Pat. No. 7,368,050.

(60) Provisional application No. 60/556,644, filed on Mar. 26, 2004.

(51) Int. Cl.
*G01N 17/04* (2006.01)
(52) U.S. Cl. .................... 205/775.5; 204/404
(58) Field of Classification Search ............ 205/775.5, 205/776.5, 776; 204/404
See application file for complete search history.

(56) References Cited

U.S. PATENT DOCUMENTS 4,130,464 A * 12/1978 Kanno et al. ............... 205/777

| 5,139,627 | A |   | 8/1992 | Eden et al. |
| 5,425,867 | A | * | 6/1995 | Dawson et al. .............. 204/400 |
| 5,888,374 | A |   | 3/1999 | Pope et al. |
| 6,280,603 | B1 |  | 8/2001 | Jovancicevic |
| 7,368,050 | B2 | * | 5/2008 | Jovancicevic et al. .... 205/775.5 |
| 2005/0211570 | A1 | | 9/2005 | Jovancicevic et al. |

FOREIGN PATENT DOCUMENTS

GB  2 218 521 A  11/1999

OTHER PUBLICATIONS

Scully, "Polarization Resistance Method for Determination of Instantaneous Corrosion Rates," Corrosion—vol. 56, No. 2, published in 2000.*

(Continued)

*Primary Examiner*—Alex Noguerola
(74) *Attorney, Agent, or Firm*—Mossman Kumar & Tyler PC

(57) ABSTRACT

An electrochemical noise method, apparatus and system calculates parameters of interest related to corrosion rates of an electrically conductive article. The method involves placing a test electrode, a reference electrode, and an auxiliary electrode in an environment of interest; placing the test electrode under potentiostatic control regime for a potential scan; measuring the relationship of current v. potential (polarization resistance, $R_p$) of the test electrode relative to the reference electrode during a first period; switching from potentiostatic control to the open circuit potential (OCP) of the test electrode; monitoring the OCP of the test electrode during a second period; determining $\Delta I$ from the relationship $R_p = \Delta V/\Delta I$, where $\Delta V$ is measured over a second period of time; and calculating the localized corrosion from the measured potential and current data.

14 Claims, 2 Drawing Sheets

OTHER PUBLICATIONS

B. H. Vassos, et al., Electroanalytical Chemistry, 1983, pp. 230-235, Wiley-Interscience, NY.

J. L. Dawson, et al., "Electrochemical Measurements for Inhibitor Assessments," Corrosion 93, NACE Annual Conference and Corrosion Show, Paper No. 108, 1993, pp. 108/1-108/19.

H.S. Isaacs, et al., "Potential Transients, Transmission and Electrochemical Corrosion Detection," Brookhaven National Labs Conference Proceedings (BNL-48707, Conf-9309150), 1993.

P.C. Searson, et al., "Analysis of Electrochemical Noise Generated by Corroding Electrodes Under Open-Circuit Conditions," J. Electrochem. Soc., vol. 135, No. 8, pp. 1908-1915, Aug. 1988.

* cited by examiner

QUANTITATIVE, REAL TIME MEASUREMENTS OF LOCALIZED CORROSION EVENTS

CROSS-REFERENCES TO RELATED APPLICATIONS

This application is a Continuation-in-Part application of U.S. patent application Ser. No. 11/086,191 filed Mar. 21, 2005, now U.S. Pat. No. 7,368,050 which in turn claims the benefit of U.S. Provisional Patent Application No. 60/556,644 filed on Mar. 26, 2004, both which are incorporated herein by reference in their entirety.

BACKGROUND

1. Technical Field

The present invention relates to electrochemical methods and systems for calculating corrosion rate, particularly to methods and techniques for evaluating localized corrosion, and most particularly relates in a non-limiting embodiment, to methods and techniques for calculating localized corrosion in hydrocarbon pipelines, transportation systems, processing vessels and fluid handling equipment.

2. Description of the Related Art

Localized corrosion of equipment is a serious problem in many industries and processes. In particular, corrosion failures in many oil and gas production systems, oil/gas/water transmission pipelines, petrochemical and chemical processing plants, fossil fuel and nuclear power plants involve localized corrosion. Localized corrosion may result in loss of production, increase in maintenance cost, environmental pollution and potential health and safety hazards, etc. It is important that the occurrence of localized corrosion is identified and the severity determined in advance of structural failure, particularly catastrophic failure. In addition, the ability of chemicals to inhibit localized corrosion needs to be determined.

Localized corrosion is the selective removal of metal by corrosion at small areas or zones on a metal surface in contact with a corrosive environment, usually a liquid. While pitting is a localized corrosion, the locally corrosive pits may eventually cover substantial portions of a corroded electrically conductive article's surface. Localized corrosion may occur when small local sites are attacked at a much higher rate than the rest of the surface. Alternatively, a film or surface may protect the majority of the structure, where a relatively small area is under localized corrosion attack. Localized corrosion occurs when corrosion works with other destructive forces such as stress, fatigue, erosion and chemical attacks. Localized corrosion can cause more damage than any of these destructive forces individually.

The problems resulting from localized corrosion have been dealt with for many years with variable success. Localized corrosion is highly stochastic in nature and its occurrence is fairly unpredictable. Thus, it is critical that statistical analysis is carried out when studying or monitoring localized corrosion. Currently, localized corrosion is studied or monitored by measuring directly large features (e.g. pits) on the surface by using standard optical microscopy with limited spatial resolution. Indirect methods are also used, such as electrochemical noise, to provide indication of the probability of localized (e.g. localization index) corrosion.

Electrochemical noise (ECN) may be defined as the spontaneous fluctuations of current and potential generated by corrosion reactions. Various methods have been used to determine corrosion rates, including a linear polarization resistance (LPR) method. In LPR a direct current (DC) signal is applied to a corroding cell consisting of two or three electrodes and the resulting DC polarization is monitored. Provided that the applied current is small and that the potential shift is less than 20 millivolts (mV), the response is linear in most cases and the measured resistance, commonly known as the polarization resistance, may be related inversely to the rate of the uniform corrosion attack. Other techniques include the application of electrochemical impedance spectroscopy (EIS) in which a sine wave current or potential is applied. In a similar manner to the linear polarization technique, and the sine wave potential or current resulting from the applied current or potential is monitored. Alternatively, a pseudo random noise signal can be applied to a corroding cell, with the electrochemical impedance obtained by time or frequency domain transformations.

Although the above techniques are widely employed, they (1) possess limitations in that they only provide information on uniform (general) corrosion conditions because they provide an average signal for the surface of the electrode being monitored; and (2) depending upon the environment, metallic material, and corrosion type, the assumption that the corrosion rate is inversely proportional to the measured charge transfer or polarization resistance is invalid because the corrosion is of a localized nature. These problems have been addressed by monitoring localized corrosion via the utilization of electrochemical potential noise analysis. Alternatively, by coupling current analysis with electrochemical potential noise analysis further information can be obtained. For example, two similar electrodes can be coupled together via a zero resistance ammeter with the output of the zero resistance ammeter passed to the input of the electrochemical noise analysis system. In this way, the fluctuation of the coupling current may be analyzed in essentially a similar manner as for the electrochemical potential noise analysis described previously.

Systems which employ two working electrodes fabricated with the same material and exposed to the same corrosion conditions as the metallic surface to be tested are known. Such systems further employ a device for measuring the coupling current between the working electrodes, a device for measuring electrochemical potential noise originating from the electrodes, and a device for comparing the coupling current with the electrochemical current noise to provide an output indicative of the degree to which corrosion is localized. The systems utilize open circuit potential conditions, employing two working electrodes in an electrolyte environment wherein both electrodes are short circuited with a low resistance amp meter. The current between these two working electrodes is the result of corrosion occurring on them, with the measurement of the net current relating to the corrosion on both of them. Disadvantages of this system, however, range from the fact that the working electrodes need to be identical to obtain accurate readings and obtaining such identical electrodes is difficult, if not impossible. Another problem is that it is unknown which electrode is responding to reveal the corrosion, due to the fact that this system requires the use of two working electrodes which limits where such systems can be employed. Furthermore, distinguishing between various types of localized corrosion is, at minimal, difficult due to the fact that both electrodes contribute to the system response.

What is needed in the art is a simplified corrosion rate detection system and method. The methods and apparatus described herein overcome some disadvantages of the prior art by providing corrosion detection calculation capability for localized metal corrosion.

SUMMARY

In one non-limiting embodiment there is provided a method for measuring localized corrosion that includes placing a test electrode, a reference electrode, and an optional auxiliary electrode in an environment of interest. In an alternate non-limiting embodiment, the reference electrode can serve the function of the auxiliary electrode. The test electrode is placed under potentiostatic control regime for a potential scan. The relationship of current v. potential (polarization resistance, $R_p$) of the test electrode is measured relative to the reference electrode during a first period of time (which may be typically less than 30 minutes). Potentiostatic control is switched to the open circuit potential (OCP) of the test electrode. The OCP of the test electrode is monitored during a second period of time (typically 30 minutes or more). The change in current ($\Delta I$) is determined from the relationship $R_p=\Delta V/\Delta I$, where $\Delta V$ is measured over the duration of the second period of time. The localized corrosion is calculated from the measured potential and current data. In most expected embodiments, this procedure or these steps will be repeated at least once.

In another non-limiting embodiment there is provided an apparatus for measuring localized corrosion that includes a test electrode; a reference electrode and optionally an auxiliary electrode, along with a device for applying a polarization to the test electrode. There is additionally provided a device for measuring current between the test electrode and the auxiliary electrode (or reference electrode, if only two electrodes are used) due to a localized corrosion event, where the current is measured substantially over the duration of the localized corrosion event. Further there is provided a device for measuring potential data between the test electrode and the reference electrode including initiation, propagation and/or repassivation (e.g. of a potential transient) due to a localized corrosion event, where the potential is measured substantially over the duration of a second period of time; and a device for calculating the localized corrosion from the measured polarization data from the relationship $R_p=\Delta V/\Delta I$, measured over the duration of a first period of time. $R_p$ is the polarization resistance of the test electrode.

Further, there is provided a localized corrosion measuring (LCM) system that involves an electrically conductive fluid contacting components including, but not necessarily limited to, a test electrode, a counter electrode, and a reference electrode. The LCM system further involves a measurement system connected to the test electrode, the auxiliary electrode, and the reference electrode. The measurement system monitors transient events indicative of localized corrosion, where the transient events are monitored between the test electrode, the auxiliary electrode and the reference electrode substantially over the duration of the transient event.

The method and apparatus of the present invention may be implemented as a set computer executable of instructions on a computer readable medium, including, but not necessarily limited to, ROM, RAM, CD-ROM, Flash RAM or any other computer readable medium, now known or unknown that when executed cause a computer to implement the functions of the present invention.

Examples of the more important features thus have been summarized rather broadly in order that the detailed description thereof that follows may be better understood, and in order that the contributions to the art may be appreciated.

There are, of course, additional features of the invention that will be described hereinafter and which will form the subject of the claims appended hereto.

BRIEF DESCRIPTION OF THE DRAWINGS

For detailed understanding, references may made to the detailed description of various disclosed embodiments, taken in conjunction with the accompanying drawings, in which like elements have been given like numerals, wherein.

DESCRIPTION OF EXEMPLARY EMBODIMENTS

Figure 1:
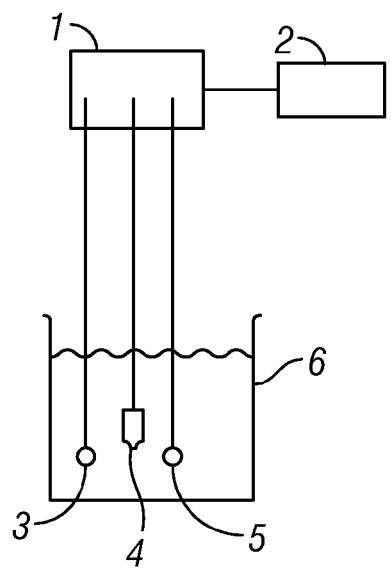
FIG. 1 is a schematic illustration of a corrosion testing apparatus of one non-limiting embodiment herein shown with three electrodes.

Methods and apparatus for the detection and characterization of the corrosion behavior in systems where localized corrosion occurs (in one non-limiting embodiment, in the form of pitting) and is quantitatively evaluated are described. The severity, frequency and time/space distribution of the localized events are determined from potential and current measurements recorded from the corroding systems.

More specifically, localized corrosion can be determined semi-quantitatively by measuring the galvanic current between two electrodes and monitoring the potential of the couple using a third reference electrode. This is typically known as current/voltage (electrochemical) noise (ECN). The technique correlates the two signals using a range of mathematical methods to calculate the general corrosion rate ($R_p=\Delta V/\Delta I$) and estimate the likelihood of localized corrosion (LI=$\sigma_i/i_{rms}$), where LI refers to Localization Index, $\sigma_i$ refers to the change in current, and $i_{rms}$ refers to the root mean square of the current. The current analysis of localized corrosion based on electrochemical noise provides indications of the likelihood of localized corrosion (LI) without specific reference to the surface affected, or the number and distribution of those localized events. LI relates to the degree of localized corrosion compared to general corrosion, i.e., the greater the LI the higher the probability of localized corrosion. However, the polarization caused by coupling the two galvanically coupled electrodes takes away a measure of sensitivity in the technique as the two galvanically coupled electrodes are not at their individual rest potentials. This polarization can make it less apparent to identify individual localized events. Localized events can occur on any one of the two electrodes which in some way contributes to the noise element of the data and a measure of inaccuracy when it comes to analysis.

Another method that gives an indication of localized corrosion is by monitoring the potential of a single test electrode with respect to a reference electrode, known as potential noise. This method can detect potential excursions caused by localized events, however without any current information it is not realistically possible in real time to correlate the significance or magnitude of a potential transient in terms of metal loss.

The Localized Corrosion Monitoring (LCM) technique herein was developed by switching between periods of potential monitoring and potentiostatic control at the rest potential. During the potentiostatic measurement the polarization of the test electrode is minimized and both current and potential data are obtained. It is possible to identify individual localized events (i.e. transients) through the reconstruction of current transients. This enables a quantitative measure of the amount of current involved in each event to be obtained, leading to possibilities of measuring the rate of localized corrosion associated with each transient (i.e. pit growth). The LCM technique depends on the analysis of data due to the regular switching between free potential measurement and polarization at the rest potential. Such signals can lead to current transient truncation and thus a possible underestimation of the total charge in each pitting event, i.e. pit depth estimation.

The present methods and apparatus provide for continuous localized corrosion monitoring and real time analysis of the monitored data. Realtime system monitoring of the corrosion status of operating equipment is enabled. In laboratory investigations, the invention provides information on localized corrosion behavior that may be directly correlated with corrosion attacks.

This apparatus and method herein provide continuous monitoring of the sudden changes in the corrosion potential with time and can provide information about localized corrosion rate and processes. These changes develop dynamically in the form of transient responses in potential transient measurements. While numerous methods have been used to measure general corrosion (e.g. linear polarization resistance (LPR), electrical resistance, EIS, electrochemical noise (ECN)), there have been few analysis methods for characterizing localized corrosion.

U.S. Pat. No. 6,280,603 to Jovancicevic discloses a potentiostatic electrochemical noise (P-ECN) invention and provides quantitative measure of localized corrosion in terms of type, frequency, distribution and penetration rate. (this patent is hereby fully incorporated herein by reference). Three different types of single current/potential transients may be identified: (i) initiation/propagation (Type I), (ii) initiation/partial repassivation (Type II), (iii) and initiation/repassivation (Type III), and one multiple initiation/propagation (Type IV) transients are recorded over time (FIG. 1 in Jovancicevic). The transients may be defined as a sudden cathodic shift in potential or anodic shift in current at open-circuit or constant potential, respectively. For a given system of objects to be monitored, depending on the metal or material examined, a transient may be a potential shift of $\geqq 0.5$ mv/sec or an anodic shift of $>0.1$ $\mu A/cm^2$/sec. For some typical systems, the Type I and II transients may be chosen as transients that last, for example, $\leqq 5$ seconds, while Type III transients may be chosen as those that last between $\geqq 30$ seconds and 200 seconds, and Type IV as those that last $\geqq 200$ seconds. The relative differences of the amplitudes and frequencies of various transients may be indicative of the types of corrosive attacks present in any active system. These electrochemical noise data can provide an indication of the type of corrosion damage occurring; and may be used to indicate the nature of localized attack. The severity of localized corrosion may be measured by the penetration rate of individual pits.

Based on the magnitude, duration and relative rate of decrease and/or increase of potential and current signals, four different types of transients can be observed in the LCM time records and classified as: Type I initiation/propagation (IP), Type II initiation/partial repassivation (IPR), Type III initiation/repassivation (IR) and Type IV initiation/repassivation/propagation (IRP) transients. Type III is of less concern because the site of the corrosion undergoes repassivation. Type IV transients are indicative of multiple pits occurring that are generally large in number, more or less active, uniformly distributed, smaller and shallower than the IP (Type I) and IPR (Type II). This transient analysis of the potential/current time dependence will be used in quantifying localized corrosion activity on the carbon steel and stainless steel tests.

The occurrence and amplitude of current/potential transients with time are directly related to the number, magnitude (depth) and distribution of localized corrosion events (e.g. pits). Thus, as the transients are longer, and as the amplitudes of the transients are larger the larger the area affected by corrosion. Also when an area affected by corrosion is larger, the depth of the corrosion is less.

By correlating data acquired from monitored systems with the above parameters, information on the severity and the feature of corrosion damage on the monitored objects can be obtained. Similarly, the effectiveness of corrosion control measures, such as chemical inhibition, or the need for such measures, can be determined.

Both potential and current LCM data may be acquired by alternatively recording with time using for example 30 seconds on (current) and 30 seconds off (potential) potentiostatic control/open circuit potential sequence. However, it is preferable the entire transient on the current and potential sides are measured to determine pitting parameters so that charge, mass and volume displaced from localized corrosion pits may be estimated. (Potential transients can be converted into equivalent current transients, e.g. by using $R_p = \Delta V / \Delta I$, by which the charge can be estimated. An alternative approach to estimate the approximate charge of a potential transient is via the double layer capacitance and potential relationship.) Therefore, operator intervention and/or software may be used to both recognize the onset of current transients (or potential transients), and to begin or resume the alternate cycling after transients have substantially terminated. LCM relies on the measurements of time of occurrence, magnitude, duration, frequency and distribution of distinct potential (negative) and current (positive) transients as a result of initiation and/or propagation/repassivation of localized corrosion events (e.g. pitting, crevice).

Localized corrosion, as indicated by the previously described transient Types I-IV, means pitting has happened locally and the extent of the event, both area and depth of penetration, may be determined directly from the current and potential measurements.

The methods and apparatus described herein make it easy to convert discrete transients in the potential fluctuations into current data. Individual localized events can be monitored in their entirety and given a meaningful current magnitude. The number of coulombs of current passed by a single transient event can be calculated and related to the magnitude of localized events (e.g. pit depth).

The potential of a test electrode is monitored with respect to a reference electrode. Periodically, a polarization is applied to the test electrode around its rest potential and $R_p$, determined using LPR, EIS, LCM or ECN, that is related to a typical potential transient caused by a localized corrosion event occurring on the test electrode, recorded. From the $R_p = \Delta V / \Delta I$ type of relationship, the resultant current response, $\Delta I$ (mirror image of the potential) is calculated and the amount of coulombs passed during the transient recorded. The base line for working out all calculations to do with potential transients is set to the Rest Potential or open circuit potential (OCP) prior to an occurring transient. Potential transients in the unpolarized data can either be detected by examination of the data or by simple automated methods as described previously. Individual data points during the potential transient may also be converted directly to current data points using the same $R_p$ relationship. The magnitude of the coulombs passed by an individual transient is directly related to metal loss caused by a localized corrosion event (see FIG. 4).

Other considerations and features of the methods and apparatus described herein include, but are not necessarily limited to the following.

The reference electrode should be resistant to localized corrosion and hold a steady potential.

The system should be used with a two electrode system, or a three electrode system, which includes a separate auxiliary electrode. In one non-limiting embodiment, a three electrode system is used. If a two electrode system is used with a combined auxiliary/reference electrode, then the combined electrode should, for a small polarization, be able to supply or absorb a much greater current then the test electrode.

The polarization is typically applied using a potentiostat, however a galvanostat or other equivalent device could be used in its place and the resultant potential response monitored.

The polarization applied should be representative of the type of transient signal produced by a localized event.

When deciding when to apply the polarization, the rate of change of free potential data should be considered such that the polarization is applied during a less active period.

Optionally, a number of polarizations may be applied to the test electrode in order to get an average response to produce a $R_p$ value for more accurate purposes.

The calibration can be used for data points prior to the periodic polarization. The calibration can be weighted from one calibration ratio to the next in order to give a smooth transition of the calibration.

The application of the periodic polarization should be only a small percentage of the total test time. One guideline is to apply the polarization every hour or at the same rate at which the conditions in the cell are expected to change, if this is more frequent.

FIG. 1 shows one non-limiting embodiment of a corrosion testing apparatus herein that includes a potentiostat 1 connected to a computer 2 (or other analyzing device) for automated control and data manipulation. Potentiostat 1 is connected to a probe arrangement including an auxiliary electrode 3, a reference electrode 4 and test or working electrode 5. All electrodes are within a cell 6 containing electrolyte, which in one non-limiting embodiment may be a corrosive liquid environment. The potentiostat 1 is able to monitor the potential of the test or working electrode 5 with respect to the reference electrode 4 over an extended time period. A typical read rate may be one measurement per second, although faster and slower measurements can be taken. The potentiostat 1 is able to control a polarization of the test or working electrode 5 with respect to the reference electrode 4 and monitor the resultant current response of the test or working electrode 5. This is done during the calibration period. Auxiliary electrode 3 measures the current.

Figure 2:
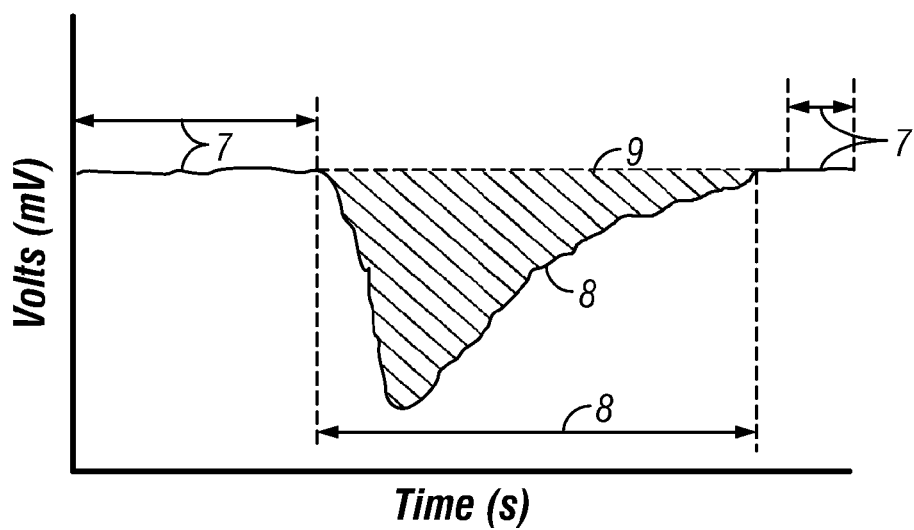
FIG. 2 is a schematic graph showing unpolarized potential data with respect to time, for a discrete potential transient shown by the shaded area 9.
Figure 3:
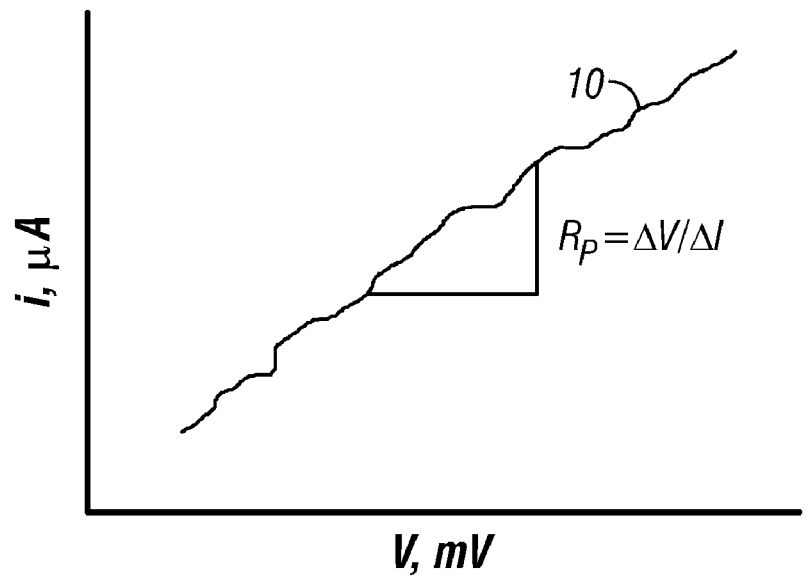
FIG. 3 is a schematic plot of current v. potential (polarization resistance ($R_p$)

FIG. 2 shows unpolarized potential and corresponding current data with respect to time, during a discrete potential transient shown by the shaded area. Potential data is recorded by the potentiostat 1 between the reference electrode 4 and the test or working electrode 5. The FIG. 2 graph shows typical background potential data 7 followed by a potential transient 8. The transient can be identified visually or by a mathematical means and the shaded area 9 calculated. Many of these transients can occur during the potential monitoring phase of the test, which may last for several hours FIG. 3 shows the current v. potential graph 10 (polarization resistance, $R_p$). The polarization is representative of a typical potential transient that can occur naturally. In the case of an expected large transient, it is helpful to use a slightly larger amplitude than a standard potential transient to reduce errors.

Figure 4:
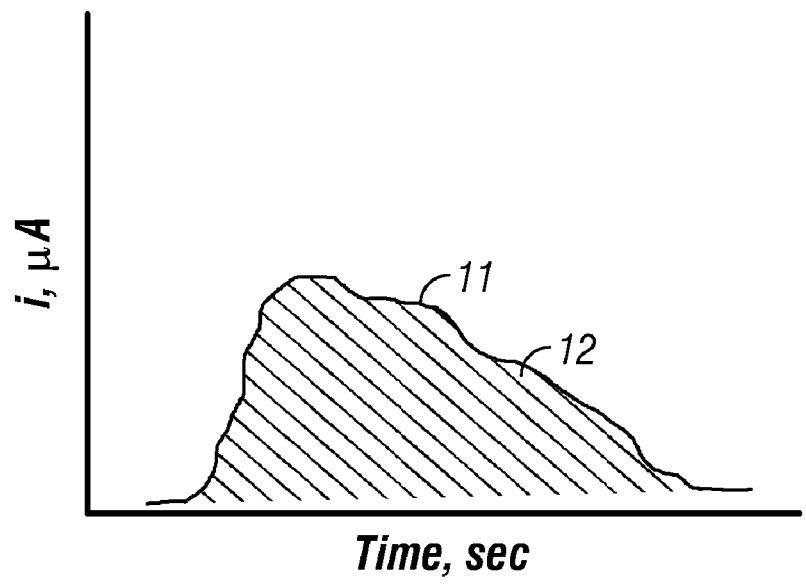
FIG. 4 is a schematic graph of a current transient (current v. time) showing the shaded area 12 for coulombs.

In FIG. 4, the current over time area 12 (coulombs—shaded area) is determined and corresponding metal loss and pit depth calculated. Curve 11 represents the current transient. Both frequency and magnitude of these events give useful information pertaining to localized corrosion.

The methods and apparatus described herein allow for determinations of changes in the rate of propagation of the depth of pits with time, or penetration rate, from the measured transients of any one of Types I-IV. Using this information the approximate mass or volume of metal corroded due to localized corrosion can be determined. The present invention therefore allows for accurate determination the number of pits that occur and their depth of penetration. The assumption that all or almost all of the corrosion is localized corrosion is strengthened by the fact that the types of corrosion described herein above, especially the "active" Type I and II transients, directly indicate ongoing localized corrosion. Without the transients that indicate localized corrosion there would be no analysis of corrosion penetration rates.

As previously mentioned, prior art techniques have measured potential and current by alternating measurements of regular periods, for example 30 seconds each. To obtain the most accurate measurements with the present invention, it is desirable to acquire measurements of the current transient throughout the time period that a pitting event occurs, and therefore the measurement of current may last considerably longer than 30 seconds. Transient event monitoring software allowing this monitoring that recognizes types of transients during their occurrence may be provided as part of methods and apparatus herein.

The present methods and apparatus provide for features including, but not necessarily limited to, an internal potentiostat, a zero resistance ammeter and internal PC (personal computer) or other computing apparatus for monitoring, measuring and analyzing data. The PC may include any operating system and run software for data analysis that accomplishes the purposes and goals described herein.

In another embodiment, the methods and apparatus are implemented as a set of computer-executable of instructions on a computer readable medium, comprising ROM, RAM, CD-ROM, Flash RAM or any other computer readable medium, now known or unknown that when executed cause a computer to implement the functions of the present invention.

The present apparatus and methods relate to measuring corrosion parameters on a metallic surface using a unique electrochemical technique.

In order to determine the corrosion rate, the working electrode may be fabricated from the same or reasonably similar material as the item of concern (i.e. the component, article), in the case of using the methods and/or apparatus to devise a technique, algorithm or program to protect an item or items of concern. Generally, the material is a metal or metal alloy. Although the auxiliary electrode can be formed of any material, including the same material as the working electrode, the auxiliary electrode may be comprised of material which is inert in the particular environment of interest. For example, the auxiliary electrode may be of a material including, but not necessarily limited to, platinum, nickel-based (e.g., Hastalloy C276), iron based (e.g., stainless steel) or a chromium-based alloy, or mixtures and alloys thereof, or any other electrically conductive, non-corrosive material. Similar to the auxiliary electrode, the reference electrode can comprise any material, but most conveniently can comprise an inert, electrically conductive material which may be the same or a different material as employed by the counter electrode.

In operation, the test or working, optional auxiliary, and reference electrodes are disposed in the same or very similar environment as the component of interest, in a spaced relation to one another. A potential between the working and reference electrodes is measured first at open circuit potential (OCP) for a certain period of time (also called a second period of time). The period of time, which can be any length of time, is typically less than 1 minute, and may be less than about 10 seconds (sec), with less than about 1 sec being convenient for reduced testing time. At the end of the period of time, a potential equivalent to the measured potential at that time is then applied to the working electrode by switching from open circuit to potentiostatic control. Once potentiostatic conditions have been established, the current between the working electrode and the auxiliary electrode can be measured for a predetermined period, also called a first period of time (although this predetermined period of time can be set to any amount of time, measurements can continue throughout the duration of a corrosion event is such an event has been detected). A new cycle can then be performed after the potentiostatic current measurement. Typically, at least one repetition is performed, although more than one may be conducted. As noted, in one non-limiting embodiment, the second period of time is longer than the first period of time, although it may be possible to practice the methods herein where the first period is longer than the second period. In an alternate, non-restrictive version, the first period may be less than 30 minutes, while the second period may be 30 minutes or more. Again, in another non-limiting embodiment, the second period may be less than 30 minutes, while the first period may be 30 minutes or more.

While various embodiments and alternatives have been shown and described, various modifications and substitutions may be made thereto without departing from the spirit and scope of the invention, which are defined only by the appended claims. Accordingly, it is to be understood that the present invention has been described by way of illustrations and not limitation. For instance, alternative devices and machines may be employed to collect and analyze the data other than those specifically mentioned.

What is claimed is:

1. A method for measuring localized corrosion comprising:
   (a) placing a test electrode and a reference electrode in proximity with one another;
   (b) placing the test electrode under potentiostatic control regime for a first period of time;
   (c) measuring the relationship of current v. potential of the test electrode relative to the reference electrode during the first period;
   (d) switching from potentiostatic control to the open circuit potential (OCP) of the test electrode;
   (e) monitoring the OCP of the test electrode during a second period of time;
   (f) determining $\Delta I$ from the relationship $R_p = \Delta V/\Delta I$, where $R_p$ is polarization resistance and where $\Delta V$ is measured over the second period of time, where (b)-(f) need not occur in the order given;
   (g) calculating the localized corrosion from the measured potential and current data; and
   (h) repeating (a) through (g) at least once.

2. The method of claim 1 where the second period is longer than the first period.

3. The method of claim 1 where the current v. potential measured in (c) is $R_p$.

4. A method for measuring localized corrosion comprising:
   (a) placing a test electrode, a reference electrode, and an auxiliary electrode in a corrosive environment;
   (b) placing the test electrode under potentiostatic control regime for a first period of time;
   (c) measuring the relationship of current v. potential of the test electrode relative to the reference electrode during the first period;
   (d) switching from potentiostatic control to the open circuit potential (OCP) of the test electrode;
   (e) monitoring the OCP of the test electrode during a second period of time;
   (f) determining $\Delta I$ from the relationship $R_p = \Delta V/\Delta I$, where $R_p$ is polarization resistance and where $\Delta V$ is measured over the second period of time, where (b)-(f) need not occur in the order given;
   (g) calculating the localized corrosion from the measured potential and current data; and
   (h) repeating (a) through (g) at least once.

5. The method of claim 4 where the second period is longer than the first period.

6. The method of claim 4 where the current v. potential measured in (c) is $R_p$.

7. The method of claim 4 where the localized corrosion is selected from the group consisting of: i) occurrence of individual localized corrosion, ii) the duration of corrosion events, iii) surface area of a pit associated with the corrosion event, iv) depth of penetration of a pit associated with the corrosion event, v) rate of penetration of a pit associated with the corrosion event, vi) volume of metal displaced by the corrosion event and vii) a type of localized corrosion event.

8. The method of claim 4 further comprising estimating a rate of penetration of a pit associated with the localized corrosion from a time rate of change of the measured potential and current data.

9. The method of claim 4 where the potential and current data are collected by electrochemical impedance (EIS), electrical resistance, linear polarization resistance (LPR), electrochemical noise (ECN), and combinations thereof.

10. A method for measuring localized corrosion comprising:
    (a) placing a test electrode, a reference electrode, and an auxiliary electrode in a corrosive environment;
    (b) placing the test electrode under potentiostatic control regime for a first period of time;
    (c) measuring the relationship of current v. potential of the test electrode relative to the reference electrode during the first period;
    (d) switching from potentiostatic control to the open circuit potential (OCP) of the test electrode;
    (e) monitoring the OCP of the test electrode during a second period of time;
    (f) determining $\Delta I$ from the relationship $R_p = \Delta V/\Delta I$, where $R_p$ is polarization resistance and where $\Delta V$ is measured over the second period of time longer than said first period of time; and
    (g) calculating the localized corrosion from the measured potential and current data, where the localized corrosion is selected from the group consisting of: i) occurrence of individual localized corrosion events, ii) the duration of corrosion events, iii) surface area of a pit associated with the corrosion event, iv) depth of penetration of a pit associated with the corrosion event, v) rate of penetration of a pit associated with the corrosion event, vi) volume of metal displaced by the corrosion event and vii) a type of localized corrosion event.

11. An apparatus for measuring localized corrosion comprising:
- (a) a test electrode;
- (b) a reference electrode;
- (c) a device for applying a polarization to the test electrode;
- (d) a device for measuring current transient data between the test electrode and the reference electrode until initiation of a current transient due to a localized corrosion event, wherein the current transient is measured substantially over a first period of time;
- (e) a device for measuring potential between the test electrode and the reference electrode including phenomena selected from the group consisting of initiation, propagation and repassivation of a potential transient due to a localized corrosion event, wherein the potential transient is measured substantially over a second period of time; and
- (f) a device for calculating the localized corrosion from the measured polarization data from the relationship $R_p = \Delta V/\Delta I$, measured over the first period of time, and $R_p$ is the polarization resistance of the test electrode.

12. The apparatus of claim 11 where the second period is longer than the first period.

13. The apparatus of claim 11 where the localized corrosion is selected from the group consisting of: i) the number of corrosion events, ii) the duration of corrosion events, iii) surface area of a corrosion event, iv) depth of penetration of a corrosion event, v) rate of penetration of a pit associated with the corrosion event, vi) volume of metal displaced by corrosion event and vii) the type of localized corrosion event.

14. The apparatus of claim 11 where the localized corrosion is a rate of penetration of a pit associated with the localized corrosion event estimated from a measured rate of change of the open circuit (free) potential and a measured current v. potential relationship.

* * * * *